United States Patent [19]
Moffatt

[11] Patent Number: 5,770,718
[45] Date of Patent: Jun. 23, 1998

[54] GENE FOR APRT FROM PLANT TISSUE

[75] Inventor: Barbara Moffatt, Waterloo, Canada

[73] Assignee: University of Waterloo, Waterloo, Canada

[21] Appl. No.: 447,010

[22] Filed: May 22, 1995

Related U.S. Application Data

[63] Continuation of Ser. No. 230,695, Apr. 21, 1994, abandoned, which is a continuation of Ser. No. 888,132, May 26, 1992, abandoned.

[30] Foreign Application Priority Data

May 23, 1991 [GB] United Kingdom .................. 9111126

[51] Int. Cl.$^6$ .......................... C12N 15/54; C12N 15/29; C12N 9/10; C12N 9/12
[52] U.S. Cl. ...................... 536/23.2; 536/23.6; 536/24.1; 435/172.3; 435/193; 435/194
[58] Field of Search .................................. 536/23.6, 24.5; 935/33, 35, 44, 45, 46; 800/205; 435/172.3, 194

[56] References Cited

FOREIGN PATENT DOCUMENTS

| 0329308 | 8/1989 | European Pat. Off. . |
|---|---|---|
| 0344029 | 11/1989 | European Pat. Off. . |
| 0412911 | 2/1991 | European Pat. Off. . |

OTHER PUBLICATIONS

R. Reiger et al., Glossary of Gen. & Czogen., 4th Ed., Springer–verlag (Berlin) p.33 1976.
R.Barnes et al., Glossary of Crop Sci. Journal, CSSA, Inc., (Madison) 1992, p. 49.
B. Moffatt, Arch. Biochem. Biophysics, vol. 283 #2 (Dec.'90) pp. 484–490.
R. Aebersold, et al., PNAS, vol. 84 (Oct. 1987)) pp. 6970–6974.
R. Mantel et al., Gene, vol. 94 ('90) pp. 181–187.
J. Sawbrook et al., "Molec. Cloning", CSH Lab Press (CSH NY) 1989, pp. 11.2–11.19,11.45–11.49,11.52–11.61.
W, Schuch et al., from "Genet. Engin. of Crop Pl.", (Ed. by Lycett et al., Butterworths, (London) ('90) pp. 221–230.
D. Grierson et al., from "Genet. Engin. of Crop Pl.", (London) ('90) pp. 115–125.
M. Koizumi et al., FEBS Lett., vol. 239(2) (88) pp. 285–288.
Schuch et al., fr. "Genet. Eng. of Crop Plants" Ed. by Lycett et al., Butterworths, London ('90) pp. 221–230.
Johnson et al, Gene 59:77–86 (1987).
Hein, Meth. Enzym. 183: 626–644 (1990).
Wilson et al, J. Biol. Chem. 261:13677–13683 (1986).
Okada et al, Biochim. BIophy. Acta 884: 304–310 (1986).
Hochstadt–Ozer et al, J. Biol. Chem. 246: 5294–5303 (1971).
Arnold et al, Meth. Enzymol. 51: 568–574 (1978).
Dayoff et al., Atlas of Protein Sequence and Structure, vol. 5, suppl. 3 (1978).
Heidecker et al, Ann. Rev. Plant Physiol. 37: 439–466 (1986).
Hunt et al, Plant Mol. Biol. 8: 23–25 (1987).
Sikela et al, Gene 22: 219–228 (1983).
Dush et al, Proc. Natl. Acad. Sci. USA 82: 2731–2735 (1985).
Nalbantoglu et al, Nucl. Acid Res. 14: 1914 (1986).
Hidaka et al, Nucl. Acid Res. 15: 9086 (1987).
Broderick et al, Proc. Natl. Acad. Sci. USA 84: 3349–3353 (1987).
Stambrook et al, Somatic Cell Mol. Genet. 10: 359–367 (1984).
Hershey et al, Gene 43:287–293 (1986).
Hershey et al, Gene 19: 89–92 (1982).
Moffatt et al, Arch. Biochem. Biophys. 283: 484–490 (1990).
Pearson et al, Proc. Natl. Acad. Sci. USA 85: 2444–2448 (1988).
Feng et al, Meth. Enzym. 183: 375–387 (1990).
Doolittle et al, Meth. Enzym. 183: 659–669 (1990).
Saitou et al, Mol. Biol. Envol. 4: 406–425 (1987).
Haughn et al, Mol. Gen. Genet. 204: 430–434 (1986).
Lahners et al, Plant Physiol. 88: 741–746 (1988).
Leutwiler et al, Mol. Gen.Genet. 194: 15–23 (1984).
Federoff et al, J. Mol. App. Genet. 2: 11–30 (1983).
Feinberg et al, Anal. Biochem. 137: 266–267 (1984).

Primary Examiner—Charles C. P. Rories
Attorney, Agent, or Firm—Sim & McBurney

[57] ABSTRACT

A cDNA for apt from a plant, particularly *A. thaliana* has been isolated, purified and characterized. The cDNA is useful for the generation of APRT-deficient mutants and as a probe for APRT cDNAs in other plants.

6 Claims, 7 Drawing Sheets

FIG.1A

```
                                                          1
                                                          CGGGTCGGGACAGTGAA
                                                                         65
ATG GCG ACT GAA GAT GTG CAA GAT CCC AGA ATC GCT AAG ATT GCC TCT
Met Ala Thr Glu Asp Val Gln Asp Pro Arg Ile Ala Lys Ile Ala Ser
          41                                                           113
TCC ATT AGA GTC ATC CCC GAC TTC CCT AAA CCA GGA ATC ATG TTT CAG
Ser Ile Arg Val Ile Pro Asp Phe Pro Lys Pro Gly Ile Met Phe Gln
          89                                                           161
GAC ATA ACG ACG CTT CTT CTC GAC ACT GAG GCC TTT AAG GAT ACT ATT
Asp Ile Thr Thr Leu Leu Leu Asp Thr Glu Ala Phe Lys Asp Thr Ile
         137                                         209
GCT TTG TTT GTT GAT AGA TAC AAA GAT AAA GGC ATA TCT GTT GTT GCA
Ala Leu Phe Cal Asp Arg Tyr Lys Asp Lys Gly Ile Ser Val Val Ala
         185                                                           257
GGT GTT GAA GCT AGA GGT TTC ATT TTT GGC CCT CCT ATT GCG TTG GCT
Gly Val Glu Ala Arg Sly Phe Ile Phe Gly Pro Pro Ile Ala Leu Ala
         233                                                           305
ATT GGT GCC AAA TTT GTT CCC ATG AGG AAG CCC AAG CTA CCT GGG
Ile Gly Ala Lys Phe Val Pro Met Arg Lys Pro Lys Leu Pro Gly
         281
```

FIG.1B

```
AAG GTT ATT TCG GAG GAG TAT TCG TTG GAG TAT GGA ACA GAT ACG ATT    353
Lys Val Ile Ser Glu Glu Tyr Ser Leu Glu Tyr Gly Thr Asp Thr Ile
                        329

GAG ATG CAC GTA GGT GCA GTA GAG CCT GGT GAG CGT GCT ATT ATT ATT    401
Glu Met His Val Gly Ala Val Glu Pro Gly Glu Arg Ala Ile Ile Ile
                        377

GAT GAC CTC ATT GCC ACG GGT GGG ACT CTC GCT GCA ATC CGA CTA        449
Asp Asp Leu Ile Ala Thr Gly Gly Thr Leu Ala Ala Ile Arg Leu
                        425

CTT GAA CGA GTA GGA GTG AAG ATT GTT GAA TGT GCT TGC GTA ATT GAG    497
Leu Glu Arg Val Gly Val Lys Ile Val Glu Cys Ala Cys Val Ile Glu
                        473

TTA CCA GAG CTT AAG GGA AAG GAG AAA CTA GGA GAG ACG TCG CTA TTT    545
Leu Pro Glu Leu Lys Gly Lys Glu Lys Leu Gly Glu Thr Ser Leu Phe
                        521

GTT CTT GTA AAG TCT GCT GCT TAA CAAGAAACTGGAAGAGAAGGTTATTGGATCG    600
Val Leu Val Lys Ser Ala Ala
                        569
```

FIG.1C

```
                    631                                            663
AGTGTTGATGCTATTTTTCATGTATGGTGAGACATTTTGCGTGGGATTTGATCCTTGTGTTT 694                                            726
CAACTTATCATAATTGGTTCAGACTAGAAAATGGCATTTGAATGTCAAAAAAAAAAAAAAA

729
AAA
```

FIG.3A

```
MTATAQQ---LEYLKNSIKSIQDYPKPGILFRDVTSLLEDPKAYALSIDLLVERYKNA-GITKV--VGTE
MATEDVQDPRIAKIASSIRVIPDFPKPGIMFQDITTLLLDTEAFKDTIALFVDRYKDK-GISVV--AGVE
MSPSISAEDKLDYVKSKIGEYPNFPKEGILFRDIFGALTDPKACVYLRDLLVDHIRES-APEAEIIVGLD
MA-----ESELQLVAQRSAVSPTSPSPGVLFRDISPLLKDPASFRASIRLLASHLKSTHGGKIDYIAGLD
MA-----DSELQLVEQRIRSFPDFPTPGVVFRDISPVLKDPASFRAAIGLLARHLKATHGGRIDYIAGLD
MS-----EPELKLVARRIRVFPDFPIPGVLFRDISPLLKDPDSFRASIRLLASHLKSTHSGKIDYIAGLD
         *        *  *  *                *      *

ARGFLFGAPVALGLGVGFVPVRKPGKLPRETISETYDLEYGRDQLETHVDAIKPGDKVLVVDDLLATGGT
ARGFIFGPPIALAIGAKFVPMRKPKKLPGKVISEEYSLEYGTDTIEMHVGAVEPGERAIIDDLLIATGGT
SRGFLFNLLIATELGLGCAPIRKKGKLAGEVVSVEYKLEYGSDTFELQKSAIKPGQKVVVVDDLLATGGS
SRGFLFGPSLAQELGLGCVLIRKRGKLPGPTVSASYALEYGKAELEIQKDALEPGQKVVVVDDLLATGGT
SRGFLFGPSLAQELGLGCVLIRKRGKLPGPTLWASYSLEYGKAELEIQKDALEPGQRVVVVDDLLATGGT
```

FIG.3B

```
SRGFLFGPSLAQELGVGCVLIRKQGKLPGPTVSASYSLEYGKAELEIQKDALEPGQRVVIVDDLLATGGT
 ***       *      **         ****     **    *    ***  ***  *****

IEATVKLIRRLGGEVADA-AFIINLFDLGGEQRLEKQGITSYSLVPFPGH  183 E.coli
LAAAIRLLERVGVKIVEC-ACVIELPELKGKEKLGETSL--FVLVKSAA-  183 A. thaliana
LVAATELIRKVGGVVVESLVVVMELVGLEGRKRLDGK-V--HSLIKY---  183 D. melanogaster
MCAACELLGQLQAEVVEC-VSLVELTSLKGREKLGSVPF--FSLLQYE--  180 HAMSTER
MNAACELLGRLQAEVLEC-VSLVELTSLKGREKLAPVPF--FSLLQYE--  180 HUMAN
MFAACDLLHELRAEVVEC-VSLVELTSLKGRERLGPIPF--FSLLEYD--  180 MOUSE
  *                  *  *  *       *
```

GENE FOR APRT FROM PLANT TISSUE

This is a continuation of application Ser. No. 08/230,695, filed Apr. 21, 1994, now abandoned, which itself is a continuation of application Ser. No. 07/888,132, filed May 26, 1992 now abandoned.

FIELD OF INVENTION

The present invention relates to adenine phosphoribosyl-transferase (APRT) and, in particular, to the isolation and sequencing of an intact cDNA from *Arabidopsis thaliana* for APRT.

BACKGROUND TO THE INVENTION

In most organisms, including plants, adenine nucleotides are synthesized by two routes, the de novo and salvage reaction pathways. Adenine phosphoribosyl-transferase (APRT) which is associated with the salvage pathway, catalyzes the conversion of adenine and 5-phosphoribosyl 1-pyrophosphate to adenosine monophosphate in a single step. In bacterial, animal and plant cells, APRT is expressed at low, constitutive levels allowing these organisms to reuse efficiently the adenine which may be produced as a byproduct of methionine, polyamine or nucleotide metabolism.

Adenine phosphoribosyltransferase has been widely exploited as a selectable marker for genetic and biological testing of bacterial and mammalian cells, because conditions have been defined which directly select either for or against the presence of APRT activity in these cells. It has recently been demonstrated that the selection for APRT deficiency using 2,6-diaminopurine, which has been applied to bacterial and mammalian systems, also is practical for the isolation of *Arabidopsis thaliana* APRT mutants. The reverse scheme, which selects for the germination of seeds with APRT activity, is also effective. Genetic analysis of the APRT-deficient mutants indicates that there is only one gene coding for APRT activity in *A. thaliana*. This locus is designated apt.

SUMMARY OF INVENTION

In the present invention, the cDNA for apt from *A. thaliana* was isolated for, in part, using APRT as a selection system in plants and also to provide a probe for the analysis of APRT activity and function in plant development. As far as the inventor is aware, this APRT cDNA is the first plant apt sequence to be characterized. Accordingly, in its broadest aspect, the present invention provides an isolated and purified cDNA for apt from a plant.

Comparison with previously analyzed apt sequences from other organisms indicated a definite region of homology. A molecular tree based on the known apt sequences revealed that the apt sequences from *Escherichia coli* and *A. thaliana* show a close relationship.

The cDNA for apt from *A. thaliana* is 729 nucleotides in length, of which 549 nucleotides are coding sequence and the remainder consists of untranslated 5' (17 nucleotides) are 3' regions (163 nucleotides).

BRIEF DESCRIPTION OF DRAWINGS

FIGS. 1A to 1C contains the nucleotide sequence of cDNA for adenine phosphoribosyltransferase from *Arabidopsis thaliana* (SEQ ID NO:1) and the deduced amino acid sequence (SEQ ID NO:2) with regions similar to the amino acid sequence determined by peptide sequencing indicated by underlining;

FIGS. 3A to 3B contains the amino acid sequence alignment of six APRT proteins, with the amino acid sequences for APRT from human, hamster, mouse, *D. melanogaster* and *E. coli* being cited from Johnson et al, Gene 59:77–86 (1987) SEQ ID NO:3 is the amino acid sequence for the APRT from *E. coli*, SEQ ID NO:4 is the amino acid sequence for the APRT from *A. thaliana*, SEQ ID NO:5 is the amino acid sequence for the APRT from *D. melanogaster*, SEQ ID NO:6 is the amino acid sequence for the APRT from hamster, SEQ ID NO:7 is the amino acid sequence for the APRT from human, and SEQ ID NO:8 is the amino acid sequence for the APRT from mouse. The asterisks indicate residues that are completely conserved. The underlining extends from amino acid position 61 to amino acid position 135 of the mouse APRT sequence. Three digit numbers denote amino acid sequence lengths. Dots make a similar segment that is shared between the *E. coli* and *A. thaliana* APRT sequences.

GENERAL DESCRIPTION OF INVENTION

Figure 2:
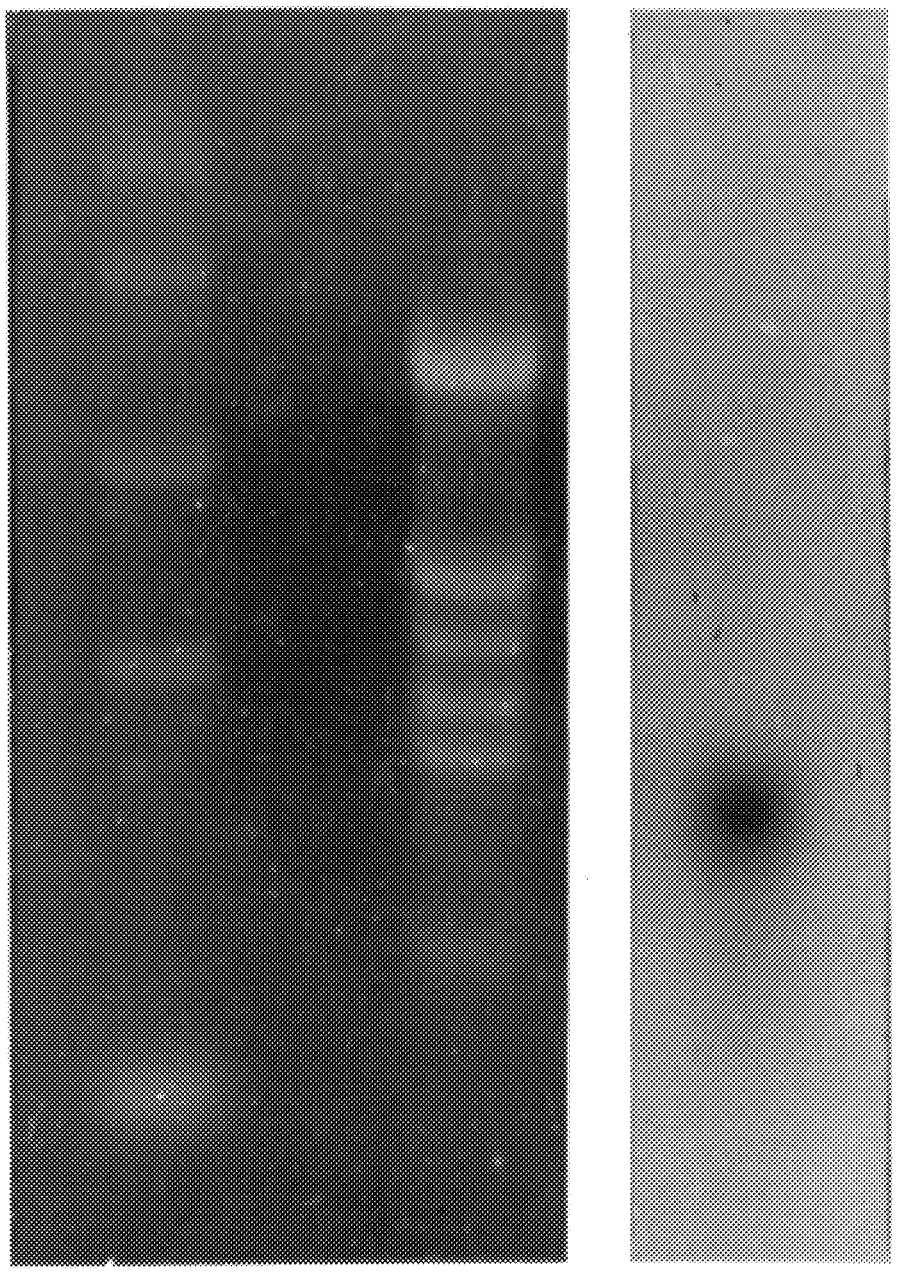
FIG. 2 contains a Northern blot analysis of *A. thaliana* RNA. Ethidium bromide stained formaldehyde gel contains in the left lane 9.5–0.24 kb RNA ladder (BRL) and 2.4 μg *A. thaliana* total RNA. Total RNA (5 μg) was probed with apt cDNA insert of pBW13.

The apt locus has been used as a selectable marker in several systems because it is possible to directly select either for or against the growth of cells with APRT activity. This type of marker also may have broad utility in plant genetic analysis. For example, a simple, clean selection is very useful to detect transposable elements, homologous recombination or monitor the efficacy of mutagenic treatments. The apt cDNA provided herein may be used to probe apt expression during plant development and isolate the corresponding gene with its associated regulatory regions.

In addition, the apt cDNA provided herein may be useful to generate APRT-deficient mutants by antisense methodologies. In the case of *A. thaliana*, this technique may involve expression of the antisense strand of the APRT cDNA in pollen tissue to reduce the translation of the APRT mRNA, thereby causing deficiency of APRT activity in this tissue and abnormal pollen development. Alternatively, the antisense strand may be modified to cause it to splice the normal APRT mRNA when introduced into pollen tissue (i.e. by ribozyme technology).

Similar mutants may be produced in other plant species using these techniques. This procedure would require the corresponding APRT cDNAs be isolated from those plants using the *A. thaliana* nucleic acid sequences as probes. These nucleic acid sequences encoding all or parts of the protein APRT then may be used to reduce or alter the pollen production of plants.

Attempts to isolate the apt cDNA via cross-hybridization with previously isolated apt sequences were unsuccessful. Although there is a 20-amino acid region which is similar in a wide range of phosphoribosyltransferases, the DNA sequence encoding these residues are not highly conserved. Within the known apt sequences, the third position of each codon within this region was sufficiently variable that it was not a useful probe to detect either *B. juncea* or *A. thaliana* apt sequences.

Previously, it was deduced that this 20 amino acid region of homology that lies, more or less, between positions 122–141 of the A. thaliana predicted amino acid sequence contains the putative binding site for the substrate, 5-phosphoribosyl-1-pyrophosphate [Wilson et al, J. Biol. Chem. 261:13677–13683 (1986)). In the human APRT, the sequence from amino acid position 122–125 is VVVV; whereas in A. thaliana (and B. juncea) APRTs it is AIII (see FIG. 1). In fact, the plant sequences identified herein differ from those in all known APRT sequences in that they lack any valine residues in this region. Apparently, the presence of valine within the putative PRPP-binding site does not correlate with the affinity of the enzyme for PRPP because the Kms for PRPP of A. thaliana, B. juncea [Okada et al, Biochim. Biophy. Acta 884: 304–310 (1986)], E. coli (Hochstadt-Ozer et al, J. Biol. Chem. 246: 5294–5303 (1971)], mouse [Okada et al, Biochim. Biophy. Acta 884: 304–310 (1986)] and human [Arnold et al, Meth. Enzymol. 51: 568–574 (1978)] are approximately 300, 36, 125, 6 and 1.2 mM respectively. Thus, it is possible that this difference reflects evolutionary change since the probability of exchange between valine and isoleucine is high [Dayhoff et al, Atlas of Protein Sequence and Structure, Vol. 5, suppl. 3 (1978)].

DESCRIPTION OF PREFERRED EMBODIMENT

The apt cDNA of A. thaliana provided in accordance with one aspect of the invention and described herein is a full-length clone, since it contains an initiating methionine and polyA tail. The good agreement between the length of the cDNA and apt mRNA determined by Northern blot analysis (see below) supports this conclusion. However, we cannot unequivocally rule out that there are 5' sequences missing from this cDNA, because there is no inframe stop codon ahead of the putative start of translation. However, there was no amino acid sequence data which could not be localized within this cDNA, consistent with there being no additional 5' translated region missing from this clone. The sequence surrounding the first AUG triplet suggests that it is the initiating codon. The consensus sequence for this region in plants is 5' N N N N A N A/U N U/A A N N N N A N N A U G C U [Heidecker et al, Ann. Rev. Plant Physiol. 37: 439–466 (1986)]. As in the consensus sequence, the apt cDNA has an A residue at position -8, a U residue at position -13 and the AUG is followed by GC with the predicted initiating dipeptide being met-ala.

The hexanucleotide AAUAAA occurs in the 3' untranslated regions of many, but not all, plant mRNAS [Hunt et al, Plant Mol. Biol. 8: 23–25 (1987)]. The 3' end of the cDNA has a run of 20 adenyl residues, but there is no obvious polyadenylation signal upstream of this region. There is an AU-rich sequence approximately 15 nucleotides ahead of the polyA tract which may fulfill this function.

Genes or cDNAs coding for APRT previously have been isolated and sequenced from several sources, including mouse [Sikela et al, Gene 22: 219–228 (1983); Dush et al, Proc. Natl. Acad. Sci. USA 82: 2731–2735 (1985)], hamster [Nalbantoglu et al, Nucl. Acid Res. 14: 1914 (1986)], humans [Hidaka et al, Nucl. Acid Res. 15: 9086 (1987); Broderick et al, Proc. Natl. Acad. Sci. USA 84: 3349–3353 (1987); Stambrook et al, Somatic Cell Nol. Genet. 10: 359–367 (1984)], Drosophila Melanogaster [Johnson et al, Gene 59: 77–86 (1987)] and Escherichia coli [Hershey et al, Gene 43:287–293 (1986); Hershey et al, Gene 19: 89–92 (1982)]. With the exception of the mouse and hamster genes, each of these apt sequences was isolated independently due to the lack of similarity among them, at the DNA level. Attempts to utilize these previously isolated apt sequences to detect the A. thaliana gene by cross-hybridization were also unsuccessful. Thus, we have taken an alternate approach, in the present invention, involving purification of APRT and amino acid sequencing in order to develop oligonucleotide probes to isolate the apt cDNA.

Since A. thaliana is a small plant, large numbers need to be grown to provide sufficient leaf tissue for enzyme purifications. To overcome this limitation, APRT was purified from another member of the Brassicacea family, namely Brassica juncea, for which both the specific activity of APRT was high and an abundant supply of leaf tissue was readily available. Once isolated, the B. juncea apt sequences were likely to be suitable probes for the isolation of the corresponding cDNA from A. thaliana.

APRT was purified from B. juncea using a procedure involving DEAE, phenyl-Sepharose, Affi-gel blue and affinity chromatography [Moffatt et al, Arch. Biochem. Biophys. 283: 484–490 (1990)]. The enzyme was judged to be homogeneous following electrophoresis of the final preparation of SDS-polyarylamide gels and silver staining. The presence of two isoforms of APRT in the preparation was indicated by isoelectric focusing analysis.

Amino acid sequencing of the purified APRT by automatic Edman degradation was not successful, suggesting that the N-terminus of the protein was blocked. Thus, samples of the APRT preparation were treated with different endoproteases and several of the resulting peptides were purified and sequenced. The results of these sequence analyses are presented in Table 1 below. Several of the peptides have regions of overlap with others and, in four places, there are apparently two possible amino acid residues (indicated in bold type in Table 1). These are likely positions which differ between the isozymes of APRT that are present in the purified preparation.

The GenBank Swiss-Prot database was searched for protein sequences similar to each of the peptides in Table 1 using the program FASTA [Pearson et al, Proc. Natl. Acad. Sci. USA 85: 2444–2448 (1988)]. In each case, the only significant identity scores were found with APRT sequences from other sources. Most often, the highest level of identity was with APRT from E. coli.

Three regions of amino acid sequence were chosen to produce degenerate oligonucleotide probes for the apt gene. The first two, designated OPM-1 and -2, were aligned to internal regions of other APRT sequences (residues 110–116 and 51–56 respectively), while the third, OPM-3, was similar to the amino acid residues near the amino terminus (residues 32–33).

OPM-1 was used to probe a cDNA library of Brassica juncea which had been constructed in the vector λgt11. Phage that contained inserts that hybridized to OPM-1 were purified and rescreened with OPM-2. Two phage were chosen for further analysis. The cDNA inserts within each of these phage were released by digestion with either EcoRl or NotI and hybridized to either OPM-1 or OPM-2 to determine the size of the inserts within each recombinant. The largest insert which hybridized to both oligonucleotides was approximately 560 bp and was subcloned into pUC119 and designated pBW5.

Sequencing of the 'EcoRl insert' of pBW5 revealed that it was a partial cDNA for adenine phosphoribosyltransferase. The deduced amino acid sequence of this fragment contained eleven of the peptide sequences of the purified protein (see Table 1 below).

The insert of pBW5 was used to rescreen the Brassica library but a larger cDNA was not detected. However, a recombinant phage carrying a different partial apt cDNA was obtained and sequenced. This clone is designated pBW9 and encoded the carboxy-terminal 52 amino acids of the purified APRT and a 120 nucleotide 3' tail (data not shown). We believe that this is a partial cDNA for the second isozyme of Brassica APRT, since the sequence of its 3' untranslated region differs from the corresponding region of pBW5. Furthermore, three of the peptide sequences of the purified APRT were found within the open reading frame predicted by the pBW9 cDNA (see Table 1 below, columns 3 and 4). In one case, the peptide within pBW9 differs in one residue from the corresponding peptide within pBW5, in exact agreement with the peptide sequencing data (compare sequences of first and second Lyc-C peptides in Table 1 below).

The larger cDNA insert of pBW5 was used to screen a cDNA library prepared from Columbia wild-type *A. thaliana*. Two different recombinant phage were recovered and subcloned into pUC119. The clone containing the largest insert was designated pBW13. The sequence of the 729 base pair cDNA insert of pBW13 is presented in FIG. 1. It has a predicted open reading frame of 183 amino acids, with a 5' untranslated region of 17 nucleotides and 3' untranslated region of 64 nucleotides. There is no obvious polyadenylation signal within the 3' region, however, a run of 20 adenyl residues is present.

Peptides that correspond to those isolated from the *B. juncea* APRT are listed in Table 1, and occur within the open reading frame (see underlined regions in FIG. 1) indicating that this is the *A. thaliana* cDNA for APRT. The amino acid sequence predicts a protein of molecular weight 27,140. This is in excellent agreement with the monomer size of APRT of *A. thaliana* which has been estimated to be 27,000, by SDS polyacrylamide gel analysis.

The presence of the initiating methionine and polyA tail in the insert suggest that the 729 bp insert in pBW 13 may be a full-length cDNA for *A. thaliana* APRT. Northern analysis of total RNA extracted from *A. thaliana* leaf tissue detected a single transcript of approximately 740 nucleotides is consistent with this conclusion (see FIG. 2).

Figure 4:
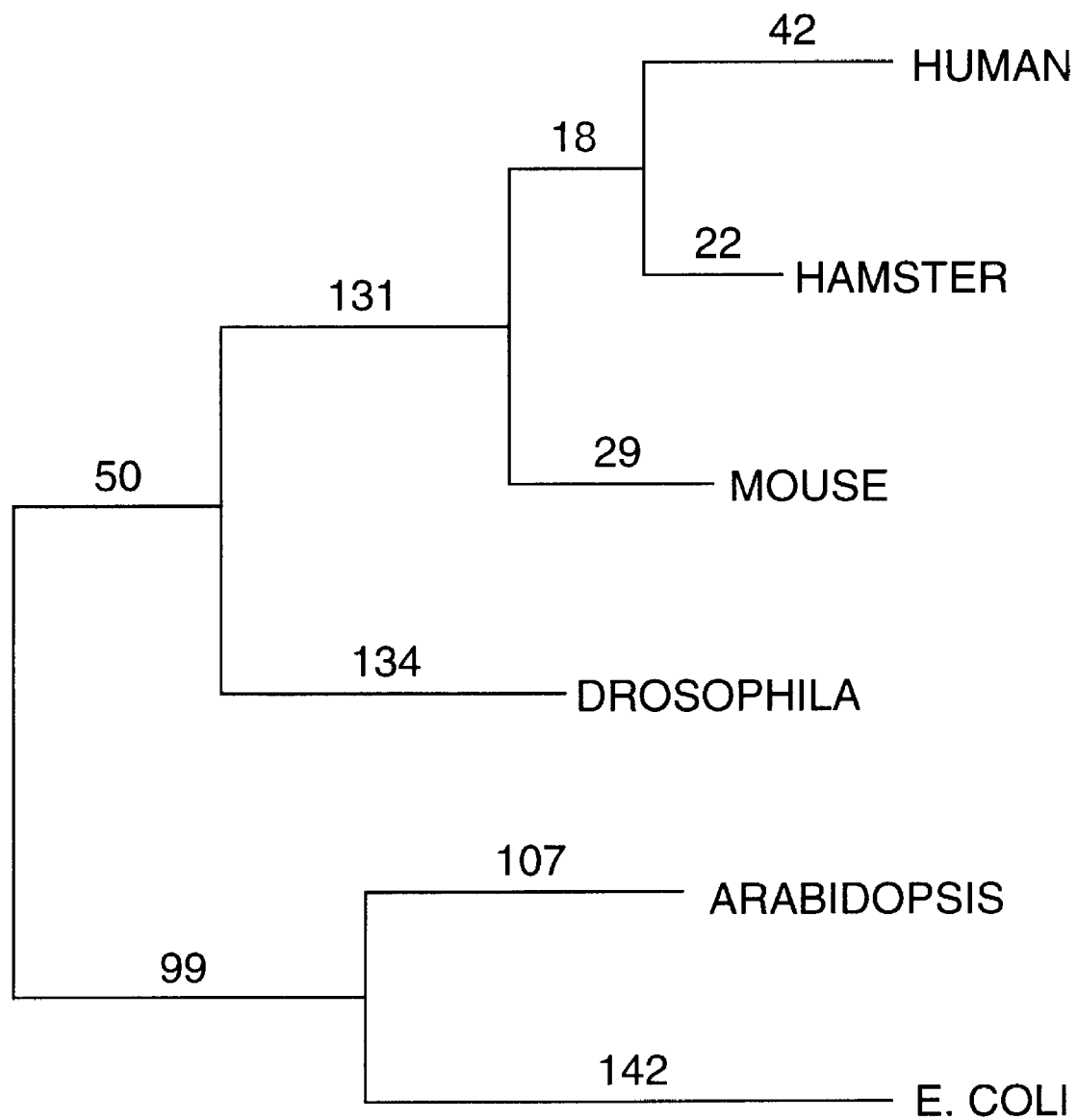
FIG. 4 shows molecular phylogeny of six APRT proteins, the APRT dendrogram, including branch lengths, being constructed using the simultaneous alignment and phylogency method of Heim, Meth. Enzym. 183: 626–644 (1990).

The alignment of six APRT sequences is shown in FIG. 3. With the mouse APRT sequence as a standard, amino acid position 61–135 (i.e. the underlined segment in FIG. 3) represents a common region among the APRT sequences with 27 of the 42 completely conserved sites falling within this span. The *A. thaliana* and *E. coli* APRT sequences are 47% similar and among the vertebrate APRT sequences the per cent similarity is 81–85% (see Table 2 below). Although the molecular trees that were constructed by different methods [Feng et al, Meth. Enzym. 183: 375–387 (1990); Doolittle et al, Meth. Enzym. 183: 659–669 (1990); Saitou et al, Mol. Biol. Evol. 4: 406–425 (1987); Hein, Moth. Enzym. 183: 626–644 (1990)] were not congruent, in each instance the *A. thaliana* and *E. coli* APRT sequences formed a separate cluster. A dendrogram for the six APRT sequences created by the 'simultaneous alignment and phylogeny construction' method of Hein, supra is presented in FIG. 4.

EXAMPLE

In developing the experimental results described above and as set forth in the Tables below and the accompanying drawings, certain materials and methods were employed, as follows:

Plant Material

*Brassica juncea* seed (Brown mustard, cv. Green Wave) purchased from Seigers Seed Co., Mich., was germinated and grown with natural light in a greenhouse at approximately 25° C. Leaves for RNA extractions were harvested after 4 to 6 weeks of growth. *A. thaliana* was grown in a 16 hour photoperiod at 22° C. and harvested as previously described by Haughn et al, Mol.Gen. Genet. 204: 430–434 (1986).

Nucleic Acid preparations

RNA was isolated from leaf tissue of three week old plants as described by Lehners et al, Plant Physiol. 88: 741–746 (1988). Genomic DNA of *A. thaliana* was isolated following the method of Leutwiler et al, Mol. Gen. Genet. 194: 15–23 (1984). Brassica DNA was isolated from young leaves by the method of Federoff et al, J. Mol. App. Genet. 2: 11–30 (1983).

Partial amino acid sequencing and oligonucleotide synthesis

APRT was purified to homogeneity as described in Moffatt et al, Arch. Biochem. Biophys. 283: 484–490 (1990). Approximately 20 µg of material eluted from the AMP-agarose column was chromatographed by reverse-phase (RP) HPLC using a Polypore Phenyl column (2.1×30 mm, Brownlee). The protein was eluted with a linear gradient (10 to 90% in 30 min) of acetonitrile in 0.1% trifluoroacetic acid. Reduction and alkylation were performed by incubating the RP-purified material in 6M guanidine-HCl, 1M Tris-HCl (pH 8.6), 10 mM EDTA, and 20 mM dithiothreitol (Calbiochem) for 1 hour at 37° C. under nitrogen. 4-Vinylpyridine (Sigma) was added to 50 mM and the incubation continued for 30 min at room temperature. The modified protein was desalted by HPLC as described above.

Digestions with sequence grade endoproteinases Asp-N and Lys-C, and with trypsin (Boehringer Manneheim) were carried out in 0.1M Tris-HCl (pH 8.5) for 16 hours at room temperature with an enzyme to substrate ratio of 1:100. Peptides from the Asp-N, Lys-c and tryptic digests were isolated by HPLC with a Vydac ODS column (2.1×150 mm, Separations Group) and eluted with a linear gradient (0–60% in 90 min) of acetonitrile in 0.1% trifluoroacetic acid.

Automated edman degradations were performed using the Applied Biosystems 477A liquid-pulse sequencer. Phenylthiohydantoin amino acids were identified on an AB1 120A PTH analyzer.

Based on the partial amino acid sequence of the purified *B. juncea* APRT, three different degenerate oligonucleotide mixtures were synthesized on a Biosearch single column Model 8600 DNA synthesizer. The oligonucleotides had the following sequences: OPM-1, GA[C,T]-AA[G,A]-AT[C,T, A]-GA[G,A]-ATG-CA[C,T]-GT; OPM-2, TT[C,T]-GT[C, G,T,A]-GA[G,A]-GA[G,A]-TA[C,T]-AA and OPM-3, GG[C,G,T,A]-AT[C,T,A]-ATG-TT[C,T]-CA[G,A]-GA.

Construction and Screening of *B. juncea* cDNA library

Five µg of polyA+ RNA from *B. juncea*, purified on an oligo-dT column [21] was used to prepare cDNA, using reagents provided in The Librarian II (Invitrogen) system, and following the manufacturers' instructions. The resulting cDNAs were ligated to NotI-EcoRI linkers, cloned into the EcoRI site of λgt11 and packaged (Gigapack Plus, Stratagene).

Approximately 3×10$^5$ primary recombinant phage were grown on 150 mm NZ-amine agar plates and transferred to nitrocellulose membranes. Filters were initially prehybridized for 3 hours at 60° C. followed by 2 hours at 37° C., in 15 ml of the following solution: 6×SSC (1×SSC=0.15M sodium chloride/0.015M sodium citrate, pH 7), 5× Denhardt's solution (50×Denhardt's solution is 5 gm Ficoll, 5 gm polyvinylpyrrolidone and 5 gm Fraction V BSA in 500 ml H$_2$O), 100 µg salmon sperm DNA (Boehringer Manneheim)/ml, 0.5% (w/v) sodium dodecyl sulfate (SDS) and 0.1% (w/v) PPi. Filters were rinsed with 6×SSC and then hybridized with 20 pmol of end-labelled oligonucleotide probe, overnight at 37° C. in 6×SSC, 5×Denhardts, 0.1% PPi, 20 µg/ml tRNA. Filters were washed in 6×SSC, 0.1% PPi with increasing temperature to 45° C. and exposed to X-AR5 film at −80° C. for 16 hours, with intensifying screens (Cronex Lightning Plus, DuPont).

Screening of A.thaliana library

Approximately 2.5×10⁵ phage from a λgt11 A.thaliana cDNA library (Clontech) were screened with the insert of pBW5 as described for B.juncea library above, except the probe was labelled by random-priming [Feinberg et al, Anal. Biochem. 137: 266–267 (1984)], to a specific activity of 6.7×10⁸ cpm/µg. Hybridization was carried out at 50° C. in: 5×SSPE (20×SSPE is 3.6 m NaCl, 200 mM NaH₂PO₄, pH 7.4, 20 mM EDTA), 5×Denhardt's solution, 0.1% SDS, 100 µg denatured salmon sperm DNA/ml and 1×10⁶ cpm probe/ml. Filters were washed with increasing stringency with the final wash being 0.2×SSPE, 0.1% SDS at 45° C. Positive plaques were identified following autoradiography overnight at −80° C. with Cronex Plus intensifying screens. Phage which hybridized strongly to this probe were plaque purified and rescreened using the same conditions.

DNA sequencing

DNA was purified from phage lysates by differential centrifugation and the EcoRI inserts cloned into pUC-119. The sequence of the inserts was determined from CsCl-purified double-stranded plasmids using a Sequenase kit (USB) and the M13 mp19 universal and reverse primers. To obtain sequence near the primer, the M13 Sequencing primer (-40) from USB was used. The nucleotide sequence data reported in this paper will appear in the EMBL, Genbank and DDBJ Nucleotide Sequence Databases under the accession number X58640 A.thaliana apt cDNA.

Northern and Southern blot analyses

Abrabidopsis and Brassica DNAs were digested with various restriction enzymes and separated by electrophoresis in 1% agarose gels (5 µg/lane). Following electrophoresis, the DNA was transferred to charged nylon membranes (Nytran, Schleicher & Schuell) in 10×SSPE. Filters were prehybridized in 5×SSPE, 5×Denhardt's solution, 0.1% SDS and 100 µg salmon sperm DNA/ml at 55° C., after which denatured probe (1×10⁶ cpm/ml) was added and filters were incubated at 55° C. for 16–24 hours. Filters were washed with increased stringency to 1×SSPE, 0.1% SDS for 30 min at 42° C.

RNA (5 µg) was electrophoresed on 1.5% agarose gels containing formaldehyde and transferred in 20×SSPE to nitrocellulose membranes. Filters were prehybridized in 5×SSPE, 2.5×Denhardt's solution, 0.1% SDS, 50% (v/v) formaimide, 100 µg salmon sperm DNA/ml for 4.5 hours at 37° C. Hybridization was carried out for 18 hours at 37° C. in 5×SSPE, 1×Denhardt's solution, 0.5% SDS and 50% formaiide containing denatured probe (>1×10⁶ cpm/ml). Nonspecifically bound probe was removed with washes of increasing stringency up to 2×SSPE, 0.5% SDS at 60° C. for 15 min, after which the filters were exposed to X-ray film.

Protein alignment and dendroaram creation

APRT sequences taken from Johnson et al, Gene 59: 77–86 (1987) and this work were aligned according to Feng and Doolittle Meth. Enzymol. 183:375–387 (1990) using a Silicon Graphics IRIX System V Release 3.3.1 operating system.

SUMMARY OF DISCLOSURE

In summary of this disclosure, an intact cDNA from Arabidopsis thaliana for adenine phosphoribosyltransferase has been isolated and sequenced. The cDNA is 729 nucleotide in length and predicts a protein molecular weight of 27,140. Modifications are possible within the scope of this invention.

TABLE 1

Amino acid sequences of isolated peptides of B. juncea APRT.

| Protease | Amino acid sequence of isolated peptides | | Present in pBW5 | pBW9 |
|---|---|---|---|---|
| Asp—N | E E Y S L E Y G T | SEQ ID NO: 9 | • | |
| | A F P K P G I M F Q | SEQ ID NO: 10 | | |
| | D T E A F K | SEQ ID NO: 11 | | |
| | D P R I P K I A S | SEQ ID NO: 12 | | |
| Trypsin | V G V T I A E - A C V I E L P V[a] | SEQ ID NO: 13 | | • |
| | V I P D F P K P G I M F O D I T[b] | SEQ ID NO: 14 | | |
| | V I S E E Y S L E Y G T D K I E M H V G A - E - GE - A[c] | SEQ ID NO: 15 | • | |
| | F V P M R | SEQ ID NO: 16 | • | |
| | L L G | SEQ ID NO: 17 | • | • |
| | I V E - A - V I E L P E L K | SEQ ID NO: 18 | • | |
| | D T I D I F V E | SEQ ID NO: 19 | | |
| Lys—C | L G E A P L F I L V T S D A | SEQ ID NO: 20 | • | |
| | L G E T P L F I L V T S D A | SEQ ID NO: 21 | | • |
| | K L P G K | SEQ ID NO: 22 | • | |
| | F V P M D L | SEQ ID NO: 23 | • | |
| | V I S E E Y S L E Y G T D | SEQ ID NO: 24 | • | |
| | I S V V A G V E A | SEQ ID NO: 25 | • | |
| | E D G Q D | SEQ ID NO: 26 | | |
| | E D V Q D P R I P K | SEQ ID NO: 27 | | |
| | D T I D I F V E E Y K[d] | SEQ ID NO: 28 | | |
| | I V E - A - V I E L P E L K | SEQ ID NO: 29 | • | |

Notes:
[a]Residues in bold type are those which differ in corresponding positions of the isolated peptides.
[b,c,d]Underlined residues indicate sequences chosen for oligonucleotide probes, [b]is OPM-3; [c]is OPM-1; [d]is OPM-2.

TABLE 2

Sequence similarity (%) among six adenine phosphoribosyltransferase proteins.

|            | E. coli | hamster | human | mouse | Arabidopsis |
|------------|---------|---------|-------|-------|-------------|
| E. coli    |         |         |       |       |             |
| hamster    | 43      |         |       |       |             |
| human      | 43      | 86      |       |       |             |
| mouse      | 44      | 85      | 81    |       |             |
| Arabidopsis| 47      | 41      | 43    | 44    |             |
| Drosophila | 45      | 49      | 46    | 49    | 39          |

---

What I claim is:

1. An isolated and purified cDNA from a plant which is the coding sequence for adenine phosphoribosyltransferase (APRT) of the plant, wherein said plant is *Arabidopsis thaliana*.

2. An isolated and purified cDNA from *Arabidopsis thaliana* which is the coding sequence for the corresponding adenine phosphoribosyltransferase (APRT) contained in the nucleotide sequence shown in FIG. 1 (SEQ ID No:1).

3. An isolated and purified cDNA which is complementary to an mRNA encoding adenine phosphoribosyltransferase (APRT) from a plant of the family Brassicacae.

4. The cDNA of claim 3 wherein said plant of the family Brassicacae is *A. thaliana*.

5. The cDNA of claim 2 further including the untranslated 5' and 3' regions of the coding sequence contained in the nucleotide sequence shown in FIG. 1 (SEQ ID No: 1).

6. An isolated and purified cDNA from *Arabidopsis thaliana* having the nucleotide sequence encoding the adenine phosphoribosyltransferase (APRT) having the deduced amino acid sequence of FIG. 1 (SEQ ID NO: 2).

\* \* \* \* \*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 729 base pairs
        ( B ) TYPE: nucleic acid
        ( C ) STRANDEDNESS: double
        ( D ) TOPOLOGY: both ( i i ) MOLECULE TYPE: DNA (genomic)

( i x ) FEATURE:
        ( A ) NAME/KEY: CDS
        ( B ) LOCATION: join(18..569)

( x i ) SEQUENCE DESCRIPTION: SEQ ID NO:1:

```
CGGGTCGGGA CAGTGAA ATG GCG ACT GAA GAT GTG CAA GAT CCC AGA ATC           50
                    Met Ala Thr Glu Asp Val Gln Asp Pro Arg Ile
                     1               5                      10

GCT AAG ATT GCC TCT TCC ATT AGA GTC ATC CCC GAC TTC CCT AAA CCA          98
Ala Lys Ile Ala Ser Ser Ile Arg Val Ile Pro Asp Phe Pro Lys Pro
             15                  20                  25

GGA ATC ATG TTT CAG GAC ATA ACG ACG CTT CTT CTC GAC ACT GAG GCC         146
Gly Ile Met Phe Gln Asp Ile Thr Thr Leu Leu Leu Asp Thr Glu Ala
         30                  35                  40

TTT AAG GAT ACT ATT GCT TTG TTT GTT GAT AGA TAC AAA GAT AAA GGC         194
Phe Lys Asp Thr Ile Ala Leu Phe Val Asp Arg Tyr Lys Asp Lys Gly
     45                  50                  55

ATA TCT GTT GTT GCA GGT GTT GAA GCT AGA GGT TTC ATT TTT GGC CCT         242
Ile Ser Val Val Ala Gly Val Glu Ala Arg Gly Phe Ile Phe Gly Pro
 60                  65                  70                  75

CCT ATT GCG TTG GCT ATT GGT GCC AAA TTT GTT CCC ATG AGG AAG CCC         290
Pro Ile Ala Leu Ala Ile Gly Ala Lys Phe Val Pro Met Arg Lys Pro
             80                  85                  90

AAG AAG CTA CCT GGG AAG GTT ATT TCG GAG GAG TAT TCG TTG GAG TAT         338
Lys Lys Leu Pro Gly Lys Val Ile Ser Glu Glu Tyr Ser Leu Glu Tyr
             95                 100                 105

GGA ACA GAT ACG ATT GAG ATG CAC GTA GGT GCA GTA GAG CCT GGT GAG         386
Gly Thr Asp Thr Ile Glu Met His Val Gly Ala Val Glu Pro Gly Glu
        110                 115                 120
```

| | | | | | | | | | | | | | | | |
|---|---|---|---|---|---|---|---|---|---|---|---|---|---|---|---|
| CGT | GCT | ATT | ATT | ATT | GAT | GAC | CTC | ATT | GCC | ACG | GGT | GGG | ACT | CTC | GCT | 434
| Arg | Ala | Ile | Ile | Ile | Asp | Asp | Leu | Ile | Ala | Thr | Gly | Gly | Thr | Leu | Ala |
| 125 | | | | | 130 | | | | | 135 | | | | | |
| GCT | GCA | ATC | CGA | CTA | CTT | GAA | CGA | GTA | GGA | GTG | AAG | ATT | GTT | GAA | TGT | 482
| Ala | Ala | Ile | Arg | Leu | Leu | Glu | Arg | Val | Gly | Val | Lys | Ile | Val | Glu | Cys |
| 140 | | | | 145 | | | | | 150 | | | | | 155 | |
| GCT | TGC | GTA | ATT | GAG | TTA | CCA | GAG | CTT | AAG | GGA | AAG | GAG | AAA | CTA | GGA | 530
| Ala | Cys | Val | Ile | Glu | Leu | Pro | Glu | Leu | Lys | Gly | Lys | Glu | Lys | Leu | Gly |
| | | | 160 | | | | 165 | | | | | 170 | | | |
| GAG | ACG | TCG | CTA | TTT | GTT | CTT | GTA | AAG | TCG | GCT | GCT | TAACAAGAAA | | | | 576
| Glu | Thr | Ser | Leu | Phe | Val | Leu | Val | Lys | Ser | Ala | Ala | | | | |
| | | 175 | | | | | 180 | | | | | | | | |

CTGGAAGAGA AAGGTTATTGG ATCGAGTGTT GATGCTATTT TTCATGTATG GTGAGACATT 636

TTGCGTGGGA TTTGATCCTT GTTGTTTCAA CTTATCATAA TTGGTTCAGA CTAGAAAATG 696

GCATTTGAAT GTCAAAAAAA AAAAAAAAAA AAA 729

( 2 ) INFORMATION FOR SEQ ID NO:2:

( i ) SEQUENCE CHARACTERISTICS:
  ( A ) LENGTH: 183 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

| Met | Ala | Thr | Glu | Asp | Val | Gln | Asp | Pro | Arg | Ile | Ala | Lys | Ile | Ala | Ser |
|---|---|---|---|---|---|---|---|---|---|---|---|---|---|---|---|
| 1 | | | | 5 | | | | | 10 | | | | | 15 | |
| Ser | Ile | Arg | Val | Ile | Pro | Asp | Phe | Pro | Lys | Pro | Gly | Ile | Met | Phe | Gln |
| | | | 20 | | | | 25 | | | | | 30 | | | |
| Asp | Ile | Thr | Thr | Leu | Leu | Leu | Asp | Thr | Glu | Ala | Phe | Lys | Asp | Thr | Ile |
| | | | 35 | | | | 40 | | | | | 45 | | | |
| Ala | Leu | Phe | Val | Asp | Arg | Tyr | Lys | Asp | Lys | Gly | Ile | Ser | Val | Val | Ala |
| | | 50 | | | | | 55 | | | | | 60 | | | |
| Gly | Val | Glu | Ala | Arg | Gly | Phe | Ile | Phe | Gly | Pro | Pro | Ile | Ala | Leu | Ala |
| 65 | | | | | 70 | | | | | 75 | | | | | 80 |
| Ile | Gly | Ala | Lys | Phe | Val | Pro | Met | Arg | Lys | Pro | Lys | Lys | Leu | Pro | Gly |
| | | | | 85 | | | | | 90 | | | | | 95 | |
| Lys | Val | Ile | Ser | Glu | Glu | Tyr | Ser | Leu | Glu | Tyr | Gly | Thr | Asp | Thr | Ile |
| | | | | 100 | | | | 105 | | | | | 110 | | |
| Glu | Met | His | Val | Gly | Ala | Val | Glu | Pro | Gly | Glu | Arg | Ala | Ile | Ile | Ile |
| | | | 115 | | | | | 120 | | | | | 125 | | |
| Asp | Asp | Leu | Ile | Ala | Thr | Gly | Gly | Thr | Leu | Ala | Ala | Ala | Ile | Arg | Leu |
| | | 130 | | | | | 135 | | | | | 140 | | | |
| Leu | Glu | Arg | Val | Gly | Val | Lys | Ile | Val | Glu | Cys | Ala | Cys | Val | Ile | Glu |
| 145 | | | | | 150 | | | | | 155 | | | | | 160 |
| Leu | Pro | Glu | Leu | Lys | Gly | Lys | Glu | Lys | Leu | Gly | Glu | Thr | Ser | Leu | Phe |
| | | | | 165 | | | | | 170 | | | | | 175 | |
| Val | Leu | Val | Lys | Ser | Ala | Ala | | | | | | | | | |
| | | | 180 | | | | | | | | | | | | |

( 2 ) INFORMATION FOR SEQ ID NO:3:

( i ) SEQUENCE CHARACTERISTICS:
  ( A ) LENGTH: 183 amino acids
  ( B ) TYPE: amino acid
  ( C ) STRANDEDNESS: single
  ( D ) TOPOLOGY: linear (ii) MOLECULE TYPE: peptide (xi) SEQUENCE DESCRIPTION: SEQ ID NO:3:

| Met | Thr | Ala | Thr | Ala | Gln | Gln | Leu | Glu | Tyr | Leu | Lys | Asn | Ser | Ile | Lys |
|---|---|---|---|---|---|---|---|---|---|---|---|---|---|---|---|
| 1 | | | | 5 | | | | | 10 | | | | | 15 | |
| Ser | Ile | Gln | Asp | Tyr | Pro | Lys | Pro | Gly | Ile | Leu | Phe | Arg | Asp | Val | Thr |
| | | | 20 | | | | | 25 | | | | | 30 | | |
| Ser | Leu | Leu | Glu | Asp | Pro | Lys | Ala | Tyr | Ala | Leu | Ser | Ile | Asp | Leu | Leu |
| | | | 35 | | | | | 40 | | | | | 45 | | |
| Val | Glu | Arg | Tyr | Lys | Asn | Ala | Gly | Ile | Thr | Lys | Val | Val | Gly | Thr | Glu |
| | | 50 | | | | | 55 | | | | | 60 | | | |
| Ala | Arg | Gly | Phe | Leu | Phe | Gly | Ala | Pro | Val | Ala | Leu | Gly | Leu | Gly | Val |
| 65 | | | | | 70 | | | | | 75 | | | | | 80 |
| Gly | Phe | Val | Pro | Val | Arg | Lys | Pro | Gly | Lys | Leu | Pro | Arg | Glu | Thr | Ile |
| | | | | 85 | | | | | 90 | | | | | 95 | |
| Ser | Glu | Thr | Tyr | Asp | Leu | Glu | Tyr | Gly | Thr | Asp | Gln | Leu | Glu | Ile | His |
| | | | | 100 | | | | | 105 | | | | | 110 | |
| Val | Asp | Ala | Ile | Lys | Pro | Gly | Asp | Lys | Val | Leu | Val | Val | Asp | Asp | Leu |
| | | | 115 | | | | | 120 | | | | | 125 | | |
| Leu | Ala | Thr | Gly | Gly | Thr | Ile | Glu | Ala | Thr | Val | Lys | Leu | Ile | Arg | Arg |
| | | | 130 | | | | | 135 | | | | | 140 | | |
| Leu | Gly | Gly | Glu | Val | Ala | Asp | Ala | Ala | Phe | Ile | Ile | Asn | Leu | Phe | Asp |
| 145 | | | | | 150 | | | | | 155 | | | | | 160 |
| Leu | Gly | Gly | Glu | Gln | Arg | Leu | Glu | Lys | Gln | Gly | Ile | Thr | Ser | Tyr | Ser |
| | | | | 165 | | | | | 170 | | | | | 175 | |
| Leu | Val | Pro | Phe | Pro | Gly | His | | | | | | | | | |
| | | | | 180 | | | | | | | | | | | |

(2) INFORMATION FOR SEQ ID NO:4:

(i) SEQUENCE CHARACTERISTICS:
        (A) LENGTH: 183 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

| Met | Ala | Thr | Glu | Asp | Val | Gln | Asp | Pro | Arg | Ile | Ala | Lys | Ile | Ala | Ser |
|---|---|---|---|---|---|---|---|---|---|---|---|---|---|---|---|
| 1 | | | | 5 | | | | | 10 | | | | | 15 | |
| Ser | Ile | Arg | Val | Ile | Pro | Asp | Phe | Pro | Lys | Pro | Gly | Ile | Met | Phe | Gln |
| | | | 20 | | | | | 25 | | | | | 30 | | |
| Asp | Ile | Thr | Thr | Leu | Leu | Leu | Asp | Thr | Glu | Ala | Phe | Lys | Asp | Thr | Ile |
| | | | 35 | | | | | 40 | | | | | 45 | | |
| Ala | Leu | Phe | Val | Asp | Arg | Tyr | Lys | Asp | Lys | Gly | Ile | Ser | Val | Val | Ala |
| | | | 50 | | | | | 55 | | | | | 60 | | |
| Gly | Val | Glu | Ala | Arg | Gly | Phe | Ile | Phe | Gly | Pro | Pro | Ile | Ala | Leu | Ala |
| 65 | | | | | 70 | | | | | 75 | | | | | 80 |
| Ile | Gly | Ala | Lys | Phe | Val | Pro | Met | Arg | Lys | Pro | Lys | Lys | Leu | Pro | Gly |
| | | | | 85 | | | | | 90 | | | | | 95 | |
| Lys | Val | Ile | Ser | Glu | Glu | Tyr | Ser | Leu | Glu | Tyr | Gly | Thr | Asp | Thr | Ile |
| | | | | 100 | | | | | 105 | | | | | 110 | |
| Glu | Met | His | Val | Gly | Ala | Val | Glu | Pro | Gly | Glu | Arg | Ala | Ile | Ile | Ile |
| | | | 115 | | | | | 120 | | | | | 125 | | |
| Asp | Asp | Leu | Ile | Ala | Thr | Gly | Gly | Thr | Leu | Ala | Ala | Ala | Ile | Arg | Leu |
| | | | 130 | | | | | 135 | | | | | 140 | | |

```
Leu  Glu  Arg  Val  Gly  Val  Lys  Ile  Val  Glu  Cys  Ala  Cys  Val  Ile  Glu
145                 150                      155                      160

Leu  Pro  Glu  Leu  Lys  Gly  Lys  Glu  Lys  Leu  Gly  Glu  Thr  Ser  Leu  Phe
                    165                      170                      175

Val  Leu  Val  Lys  Ser  Ala  Ala
                    180
```

( 2 ) INFORMATION FOR SEQ ID NO:5:

( i ) SEQUENCE CHARACTERISTICS:
        ( A ) LENGTH: 183 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met  Ser  Pro  Ser  Ile  Ser  Ala  Glu  Asp  Lys  Leu  Asp  Tyr  Val  Lys  Ser
1                   5                        10                       15

Lys  Ile  Gly  Glu  Tyr  Pro  Asn  Phe  Pro  Lys  Glu  Gly  Ile  Leu  Phe  Arg
                    20                       25                       30

Asp  Ile  Phe  Gly  Ala  Leu  Thr  Asp  Pro  Lys  Ala  Cys  Val  Tyr  Leu  Arg
                    35                       40                       45

Asp  Leu  Leu  Val  Asp  His  Ile  Arg  Glu  Ser  Ala  Pro  Glu  Ala  Glu  Ile
          50                        55                       60

Ile  Val  Gly  Leu  Asp  Ser  Arg  Gly  Phe  Leu  Phe  Asn  Leu  Leu  Ile  Ala
65                            70                       75                       80

Thr  Glu  Leu  Gly  Leu  Gly  Cys  Ala  Pro  Ile  Arg  Lys  Lys  Gly  Lys  Leu
                    85                       90                       95

Ala  Gly  Glu  Val  Val  Ser  Val  Glu  Tyr  Lys  Leu  Glu  Tyr  Gly  Ser  Asp
                    100                      105                      110

Thr  Phe  Glu  Leu  Gln  Lys  Ser  Ala  Ile  Lys  Pro  Gly  Gln  Lys  Val  Val
               115                      120                      125

Val  Val  Asp  Asp  Leu  Leu  Ala  Thr  Gly  Gly  Ser  Leu  Val  Ala  Ala  Thr
     130                      135                      140

Glu  Leu  Ile  Arg  Lys  Val  Gly  Gly  Val  Val  Val  Glu  Ser  Leu  Val  Val
145                 150                      155                      160

Val  Met  Glu  Leu  Val  Gly  Leu  Glu  Gly  Arg  Lys  Arg  Leu  Asp  Gly  Lys
                    165                      170                      175

Val  His  Ser  Leu  Ile  Lys  Tyr
                    180
```

( 2 ) INFORMATION FOR SEQ ID NO:6:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Met  Ala  Glu  Ser  Glu  Leu  Gln  Leu  Val  Ala  Gln  Arg  Ser  Ala  Val  Ser
1                   5                        10                       15

Pro  Thr  Ser  Pro  Ser  Pro  Gly  Val  Leu  Phe  Arg  Asp  Ile  Ser  Pro  Leu
                    20                       25                       30

Leu  Lys  Asp  Pro  Ala  Ser  Phe  Arg  Ala  Ser  Ile  Arg  Leu  Leu  Ala  Ser
               35                       40                       45
```

-continued

```
His Leu Lys Ser Thr His Gly Gly Lys Ile Asp Tyr Ile Ala Gly Leu
    50              55                  60

Asp Ser Arg Gly Phe Leu Phe Gly Pro Ser Leu Ala Gln Glu Leu Gly
65                  70                  75                  80

Leu Gly Cys Val Leu Ile Arg Lys Arg Gly Lys Leu Pro Gly Pro Thr
                85                  90                  95

Val Ser Ala Ser Tyr Ala Leu Glu Tyr Gly Lys Ala Glu Leu Glu Ile
                100                 105                 110

Gln Lys Asp Ala Leu Glu Pro Gly Gln Lys Val Val Val Val Asp Asp
        115                 120                 125

Leu Leu Ala Thr Gly Gly Thr Met Cys Ala Ala Cys Glu Leu Leu Gly
    130                 135                 140

Gln Leu Gln Ala Glu Val Val Glu Cys Val Ser Leu Val Glu Leu Thr
145                 150                 155                 160

Ser Leu Lys Gly Arg Glu Lys Leu Gly Ser Val Pro Phe Phe Ser Leu
                165                 170                 175

Leu Gln Tyr Glu
            180
```

( 2 ) INFORMATION FOR SEQ ID NO:7:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Met Ala Asp Ser Glu Leu Gln Leu Val Glu Gln Arg Ile Arg Ser Phe
1               5                   10                  15

Pro Asp Phe Pro Thr Pro Gly Val Val Phe Arg Asp Ile Ser Pro Val
                20                  25                  30

Leu Lys Asp Pro Ala Ser Phe Arg Ala Ala Ile Gly Leu Leu Ala Arg
            35                  40                  45

His Leu Lys Ala Thr His Gly Gly Arg Ile Asp Tyr Ile Ala Gly Leu
    50                  55                  60

Asp Ser Arg Gly Phe Leu Phe Gly Pro Ser Leu Ala Gln Glu Leu Gly
65                  70                  75                  80

Leu Gly Cys Val Leu Ile Arg Lys Arg Gly Lys Leu Pro Gly Pro Thr
                85                  90                  95

Leu Trp Ala Ser Tyr Ser Leu Glu Tyr Gly Lys Ala Glu Leu Glu Ile
                100                 105                 110

Gln Lys Asp Ala Leu Glu Pro Gly Gln Arg Val Val Val Val Asp Asp
        115                 120                 125

Leu Leu Ala Thr Gly Gly Thr Met Asn Ala Ala Cys Glu Leu Leu Gly
    130                 135                 140

Arg Leu Gln Ala Glu Val Leu Glu Cys Val Ser Leu Val Glu Leu Thr
145                 150                 155                 160

Ser Leu Lys Gly Arg Glu Lys Leu Ala Pro Val Pro Phe Phe Ser Leu
                165                 170                 175

Leu Gln Tyr Glu
            180
```

( 2 ) INFORMATION FOR SEQ ID NO:8:

( i ) SEQUENCE CHARACTERISTICS:

(A) LENGTH: 180 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

| Met | Ser | Glu | Pro | Glu | Leu | Lys | Leu | Val | Ala | Arg | Arg | Ile | Arg | Val | Phe |
|---|---|---|---|---|---|---|---|---|---|---|---|---|---|---|---|
| 1 | | | | 5 | | | | | 10 | | | | | 15 | |
| Pro | Asp | Phe | Pro | Ile | Pro | Gly | Val | Leu | Phe | Arg | Asp | Ile | Ser | Pro | Leu |
| | | | 20 | | | | 25 | | | | | 30 | | | |
| Leu | Lys | Asp | Pro | Asp | Ser | Phe | Arg | Ala | Ser | Ile | Arg | Leu | Leu | Ala | Ser |
| | | 35 | | | | | 40 | | | | | 45 | | | |
| His | Leu | Lys | Ser | Thr | His | Ser | Gly | Lys | Ile | Asp | Tyr | Ile | Ala | Gly | Leu |
| | 50 | | | | | 55 | | | | | 60 | | | | |
| Asp | Ser | Arg | Gly | Phe | Leu | Phe | Gly | Pro | Ser | Leu | Ala | Gln | Glu | Leu | Gly |
| 65 | | | | | 70 | | | | | 75 | | | | | 80 |
| Val | Gly | Cys | Val | Leu | Ile | Arg | Lys | Gln | Gly | Lys | Leu | Pro | Gly | Pro | Thr |
| | | | | 85 | | | | | 90 | | | | | 95 | |
| Val | Ser | Ala | Ser | Tyr | Ser | Leu | Glu | Tyr | Gly | Lys | Ala | Glu | Leu | Glu | Ile |
| | | | 100 | | | | | 105 | | | | | 110 | | |
| Gln | Lys | Asp | Ala | Leu | Glu | Pro | Gly | Gln | Arg | Val | Val | Ile | Val | Asp | Asp |
| | | 115 | | | | | 120 | | | | | 125 | | | |
| Leu | Leu | Ala | Thr | Gly | Gly | Thr | Met | Phe | Ala | Ala | Cys | Asp | Leu | Leu | His |
| | 130 | | | | | 135 | | | | | 140 | | | | |
| Glu | Leu | Arg | Ala | Glu | Val | Val | Glu | Cys | Val | Ser | Leu | Val | Glu | Leu | Thr |
| 145 | | | | | 150 | | | | | 155 | | | | | 160 |
| Ser | Leu | Lys | Gly | Arg | Glu | Arg | Leu | Gly | Pro | Ile | Pro | Phe | Phe | Ser | Leu |
| | | | | 165 | | | | | 170 | | | | | 175 | |
| Leu | Glu | Tyr | Asp | | | | | | | | | | | | |
| | | | 180 | | | | | | | | | | | | |

(2) INFORMATION FOR SEQ ID NO:9:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

| Glu | Glu | Tyr | Ser | Leu | Glu | Tyr | Gly | Thr |
|---|---|---|---|---|---|---|---|---|
| 1 | | | | 5 | | | | |

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

| Asp | Phe | Pro | Lys | Pro | Gly | Ile | Met | Phe | Gln |
|---|---|---|---|---|---|---|---|---|---|
| 1 | | | | 5 | | | | | 10 |

(2) INFORMATION FOR SEQ ID NO:11:

(i) SEQUENCE CHARACTERISTICS:
   (A) LENGTH: 6 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:11:

```
Asp Thr Glu Ala Phe Lys
1               5
```

(2) INFORMATION FOR SEQ ID NO:12:

(i) SEQUENCE CHARACTERISTICS:
   (A) LENGTH: 9 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:12:

```
Asp Pro Arg Ile Pro Lys Ile Ala Ser
1               5
```

(2) INFORMATION FOR SEQ ID NO:13:

(i) SEQUENCE CHARACTERISTICS:
   (A) LENGTH: 15 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:13:

```
Val Gly Val Thr Ile Ala Glu Ala Cys Val Ile Glu Leu Pro Val
1               5                   10                  15
```

(2) INFORMATION FOR SEQ ID NO:14:

(i) SEQUENCE CHARACTERISTICS:
   (A) LENGTH: 16 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:14:

```
Val Ile Pro Asp Phe Pro Lys Pro Gly Ile Met Phe Gln Asp Ile Thr
1               5                   10                  15
```

(2) INFORMATION FOR SEQ ID NO:15:

(i) SEQUENCE CHARACTERISTICS:
   (A) LENGTH: 25 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:15:

```
Val Ile Ser Glu Glu Tyr Ser Leu Glu Tyr Gly Thr Asp Lys Ile Glu
1               5                   10                  15
Met His Val Gly Ala Glu Gly Glu Ala
                20                  25
```

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Phe  Val  Pro  Met  Arg
1                   5
```

( 2 ) INFORMATION FOR SEQ ID NO:17:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Leu  Leu  Gly
1
```

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Ile  Val  Glu  Ala  Val  Ile  Glu  Leu  Pro  Glu  Leu  Lys
1                   5                        10
```

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Asp  Thr  Ile  Asp  Ile  Phe  Val  Glu
1                   5
```

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Leu  Gly  Glu  Ala  Pro  Leu  Phe  Ile  Leu  Val  Thr  Ser  Asp  Ala
1                   5                        10
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Leu Gly Glu Thr Pro Leu Phe Ile Leu Val Thr Ser Asp Ala
1               5                   10
```

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Lys Leu Pro Gly Lys
1               5
```

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Phe Val Pro Met Asp Leu
1               5
```

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Val Ile Ser Glu Glu Tyr Ser Leu Glu Tyr Gly Thr Asp
1               5                   10
```

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Ile Ser Val Val Ala Gly Val Glu Ala
1               5
```

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Glu Asp Gly Gln Asp
    1                   5

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Glu Asp Val Gln Asp Pro Arg Ile Pro Lys
    1               5                      10

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Asp Thr Ile Asp Ile Phe Val Glu Glu Tyr Lys
    1               5                         10

(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Ile Val Glu Ala Val Ile Glu Leu Pro Glu Leu Lys
    1               5                            10